United States Patent
Faure (10) Patent No.: US 8,317,785 B2
(45) Date of Patent: Nov. 27, 2012

(54) MEDICAL DEVICE USING A COILED ELECTRODE

(75) Inventor: André Faure, Besancon (FR)

(73) Assignee: Trod Medical, Paris (FR)

( * ) Notice: Subject to any disclaimer, the term of this patent is extended or adjusted under 35 U.S.C. 154(b) by 714 days.

(21) Appl. No.: 10/556,770

(22) PCT Filed: May 17, 2004

(86) PCT No.: PCT/BE2004/000073
§ 371 (c)(1),
(2), (4) Date: Feb. 13, 2007

(87) PCT Pub. No.: WO2004/100812
PCT Pub. Date: Nov. 25, 2004

(65) Prior Publication Data
US 2007/0179494 A1    Aug. 2, 2007

Related U.S. Application Data

(60) Provisional application No. 60/471,083, filed on May 16, 2003.

(51) Int. Cl.
A61B 18/14 (2006.01)

(52) U.S. Cl. .......................................................... 606/41

(58) Field of Classification Search .............. 606/41–45, 606/32, 34, 36–40
See application file for complete search history.

(56) References Cited

U.S. PATENT DOCUMENTS

| 5,507,743 | A | * | 4/1996 | Edwards et al. | 606/41 |
| 5,676,662 | A | * | 10/1997 | Fleischhacker et al. | 606/41 |
| 5,921,982 | A | | 7/1999 | Lesh et al. | |
| 6,165,170 | A | * | 12/2000 | Wynne et al. | 606/9 |
| 6,167,292 | A | * | 12/2000 | Badano et al. | 600/407 |
| 6,497,704 | B2 | | 12/2002 | Ein-Gal | |
| 6,638,275 | B1 | * | 10/2003 | McGaffigan et al. | 606/41 |
| 6,641,580 | B1 | * | 11/2003 | Edwards et al. | 606/41 |
| 2002/0049439 | A1 | * | 4/2002 | Mulier et al. | 606/41 |
| 2002/0147446 | A1 | * | 10/2002 | Ein-Gal | 606/41 |
| 2007/0027448 | A1 | * | 2/2007 | Paul et al. | 606/41 |

FOREIGN PATENT DOCUMENTS
WO    WO 00/35531    6/2000

* cited by examiner

*Primary Examiner* — Michael Peffley
*Assistant Examiner* — Ronald Hupczey, Jr.
(74) *Attorney, Agent, or Firm* — Reinhart Boerner Van Deuren P.C.

(57) ABSTRACT

The present invention is related to a medical device (1) adapted for the ablation of a target volume inside an anatomical organ, said medical device (1) comprising as elements a main body (2), stabilizing means (3) for stabilizing the device relatively to the organ and heating means in the form of a bipolar electrode (10) comprising parts activable by an external radiofrequency generator for heating said target volume, wherein said bipolar electrode comprises a first element having the form of a central anchoring member (5), and a second element having the form of at least two concentric rigid helices or coils (4',4",) of predetermined diameter (D) and length (L), said helices surrounding the central anchoring member (5). The present invention also concerns a surgical assembly comprising said medical device and controlling means as well as a process for the specific destruction a target volume inside an organ by means of said medical device or surgical assembly.

25 Claims, 8 Drawing Sheets

MEDICAL DEVICE USING A COILED ELECTRODE

CROSS-REFERENCE TO RELATED PATENT APPLICATIONS

This patent application is the National Stage of International Application No. PCT/BE2004/00073 filed May 17, 2004, that claims the benefit of U.S. Provisional Patent Application No. 60/471,083 filed May 16, 2003.

FIELD OF THE INVENTION

The present invention concerns the field of surgery, more particularly the field of cancer surgery and is related to a medical device or instrument.

STATE OF THE ART

Most cancer cells first develop in a primary tumor site such as the breast, colon or lung, but then cells from these cancers can spread, or metastasize, to other parts of the body where they may form new tumors.

A possible strategy for the treatment of cancer corresponds to a local treatment of the tumor, wherein cancer is attacked at a specific site. Different techniques have been developed on the basis of said strategy. Ablation surgery in order to remove tumors is certainly the most common local treatment used worldwide. However, other local treatment techniques also exist, among which is radiation therapy, wherein radioactive particles, seeds or rods implanted directly into a tumor are used. This type of radiation treatment is called brachytherapy.

New local treatment techniques such as radiofrequency (RF) ablation procedure and other similar interventional radiology catheter ablation procedures reveal to be particularly promising for patients whose cancers cannot be treated surgically.

The device used in the radiofrequency ablation technique generally comprises a needle which is placed through the skin and into the tumor. The needle is linked to a radiofrequency generator such that when a radiofrequency is sent through the needle, the needle is heated and destroys the tumor. This procedure is performed under conscious sedation and most patients can go home the same day.

RF treatment presents several advantages:
it is a new local treatment option for cancer;
it is a minimally invasive method;
its safety has been proven over many years in thousands of people;
it is less risky and has fewer complications compared to surgery;
generally, only local anesthesia is required;
it may be done as an outpatient procedure, or shorten hospital stay;
most patients can resume normal activities within a few days;
it can be repeated if necessary;
and it may be combined with other treatment options, such as chemotherapy.

However, the capabilities of RF technique are nowadays limited as there is a real technical difficulty in controlling precisely the region to be destroyed with the existing RF devices. Indeed, the conception of said devices is such that the heating of the tissues tends to propagate beyond the tumour site. In some cases, cell's dehydration stops the heating propagation and then, the treatment's effectiveness. Currently, some cooled devices and expandable electrodes allows bigger regions to be destroyed. Then, increasing the destruction volume is possible, but the precise control of the destruction region becomes to be reached. This is important in some organs where the lesion of neighbour organs and structures, like important vessels, represents a real and still unsolved problem.

Among the solutions proposed in the prior art in order to solve this problem, it has been suggested in document U.S. Pat. No. 5,507,743 to use a RF ablation device comprising a variable pitch helical electrode capable of wrapping the tumor. However, the use of said device presents a serious drawback from a practical point of view, as it is known that increasing the distance between the two poles of the electrode produces two undesirable effects. The first undesirable effect is that the physician must increase the RF generator power, so as to compensate the bigger distance to destroy. However, increasing the power heats the cells closer to the active electrode to temperatures as high as 90 or 100 Celsius degrees, dehydrating these cells and stopping the heating effect (the heating and consequently the destruction effect is propagated through the cell's water). The second undesirable effect is that more distant tissues are easily cooled by surrounding vessels, thereby increasing the risk of non destruction of all tumoral cells.

In other words, there is still a need for a satisfying device which could be used in RF ablation techniques in order to destroy by heating a tumor site inside an organ.

AIMS OF THE INVENTION

The present invention aims to provide a medical device or instrument and a process adapted for the ablation (i.e. destruction) by radiofrequency technique of a target volume, such as a tumor, located inside or at an anatomical organ such as prostate, kidney, adrenal glands, breast, lungs and pancreas, an even brain, which would not present the drawbacks of the solutions of the prior art.

In particular, the present invention aims to provide a device and a process which would ensure, in operating conditions, a total but specific destruction of a predetermined unsafe tissue volume inside or at said organ, while preserving the surrounding safe tissues.

Another aim of the present invention is to provide a device and a process which could be used or carried out both easily and securely.

SUMMARY OF THE INVENTION

The present invention is related to a medical device adapted for the ablation of a target volume inside an anatomical organ, said device comprising as elements a main body, stabilising means for stabilising the device relatively to the organ and heating means in the form of a bipolar electrode comprising parts activable by an external radiofrequency generator for heating said target volume, wherein said bipolar electrode comprises a first element having the form of a central anchoring member, and a second element having the form of at least two concentric helices of predetermined diameter and length, said helices surrounding the central anchoring member.

Advantageously, said central anchoring member may take the form of a central needle or of an extremely thin helix.

Preferably, said helices are rigid i.e. said helices are not deformable by simple external manual pressure (not deformable by direct manipulation).

Preferably, the medical device can adopt at least one rest configuration wherein the bipolar electrode is unactivable and is folded-up inside the stabilising means and the main body, and at least one working configuration wherein the bipolar electrode protrudes outside the stabilisation means so as to deploy both the anchoring member and the helices, said helices thereby forming a cage-like structure around said anchoring member, with an internal face facing the central anchoring member and an external face oriented in an opposite manner (exposed to the environment), and wherein said bipolar electrode is activable so as to have a passive pole and an active pole.

It is meant by "activation of the electrode" the circulation inside said electrode of a current of electric or electromagnetic type from one area of said electrode which forms the active pole to another area of said electrode which forms the passive pole.

According to a first preferred embodiment of the medical device, in the working configuration at least one of the helices is activable independently from the others, only on its internal face, so as to form the active pole of the bipolar electrode, while the passive pole of the bipolar electrode can be formed either by the central anchoring member or by the external face of the helix forming the active pole or by the external face of an helix of smaller diameter than the helix forming the active pole.

According to a second preferred embodiment of the medical device, in the working configuration at least one of the helices is activable independently from the others, on both its internal face and its external face, so as to form the active pole of the bipolar electrode, while the passive pole of the bipolar electrode can be formed either by the central anchoring member or by a helix of smaller diameter than the helix forming the active pole.

In the present invention, the helices of the medical device may be activable at least on one fraction of their length, and possibly on their full length.

Preferably, in the rest configuration, the device according to the invention has the following degrees of freedom in a referential system (O,X,Y,Z) centred at the centre of the main body:
  Rotation around the Z axis;
  Rotation around the Y axis;
  Translation along the X axis;
  Translation along the Y axis;
  Translation along the Z axis.

Preferably, in the working configuration, the anchoring member of the bipolar electrode has one degree of freedom in a referential system (O,X,Y,Z) centred at the centre of the main body corresponding to a translation along the X axis, while the helices have two degrees of freedom each, one corresponding to a translation along the X axis, and the other to a rotation around the X axis.

Preferably, in the working configuration any translation or rotational movement of the main body and of the stabilising means is blocked.

Preferably, the medical device of the invention is conceived such that the positioning of its different elements relatively to the target volume and relatively to each other and the activation state of said parts of the bipolar electrode are able to be controlled by controlling means.

Advantageously, said controlling means comprise a robot.

The present invention is also related to a surgical assembly comprising the medical device according to any one of the preceding claims, coupled to controlling means.

Preferably, said controlling means comprise a robot.

Preferably, the surgical assembly further comprises a 3D-navigation system. It is meant by "3D-navigation system any device able to take 3D informations on the position in real time of an object such as a camera or ultrasound measurement device (echographic navigation system).

Preferably the controlling means also comprise a computer coupled to the robot via interfacing means such as an A/D converter.

Preferably, said assembly is linked to a fixed support such as a surgical table.

Another object of the present invention is a process for the destruction of a target volume inside an anatomical organ by radiofrequency ablation technique using the medical device or the surgical assembly as disclosed above, said process comprising the following steps:
  determining parameters comprising at least the anatomical features (size, shape, position, . . . ) of the target volume to be treated;
  on the basis of said parameters, defining at least the number of helices to use in the bipolar electrode, the passive and active poles of the bipolar electrode, the sequence of activation of the bipolar electrode, and the intensity and time of activation of said bipolar electrode;
  introducing said medical device inside the patient;
  once the target organ is reached, positioning the medical device relatively to the target volume;
  performing the treatment procedure of the target tumor following the predetermined parameters.

The present invention also concerns a process for the destruction of a target volume inside an anatomical organ by radiofrequency ablation technique using the medical device or the surgical assembly disclosed hereabove.

Preferably, said process comprises the following steps:
by means of the 3D navigation system,
  establishing a surgical protocol according to different parameters including the anatomical features of the target volume to be treated, said surgical protocol defining namely the sequence and type of movements of the medical device and of its different elements, the number of helices to use in the bipolar electrode, the definition of the passive and active poles of the bipolar electrode, the sequence of activation of the bipolar electrode, the intensity and time of activation of said bipolar electrode;
  manually introducing said medical device inside the patient and approximately positioning said device relatively to the target volume;
  starting the automatic operating of the robot so as to perform the surgical procedure under automatic control following the pre-established surgical protocol;
  monitoring the surgical procedure and possibly restoring a manual control on the device, in case of security problems.

Another object of the invention concerns the use of said medical device or said surgical assembly for the treatment of a target volume inside an anatomical organ selected from the group consisting of kidneys, lungs, liver, breast, prostate and brain.

DETAILED DESCRIPTION OF THE INVENTION

Figure 1:
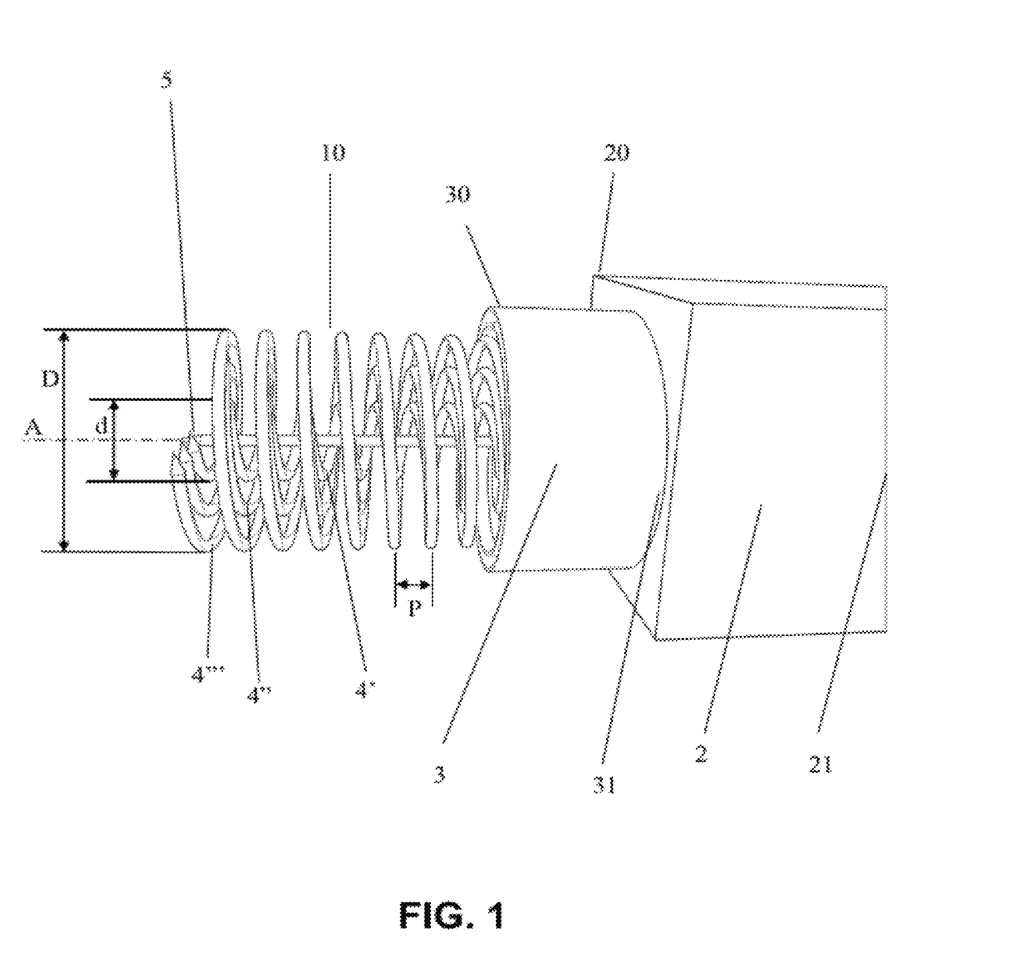
FIG. 1 represents an overview of the medical device according to the present invention.

As illustrated on FIG. 1, the medical device 1 according to the invention comprises as elements a main body 2, stabilizing means 3, and a bipolar electrode 10.

Figure 7:
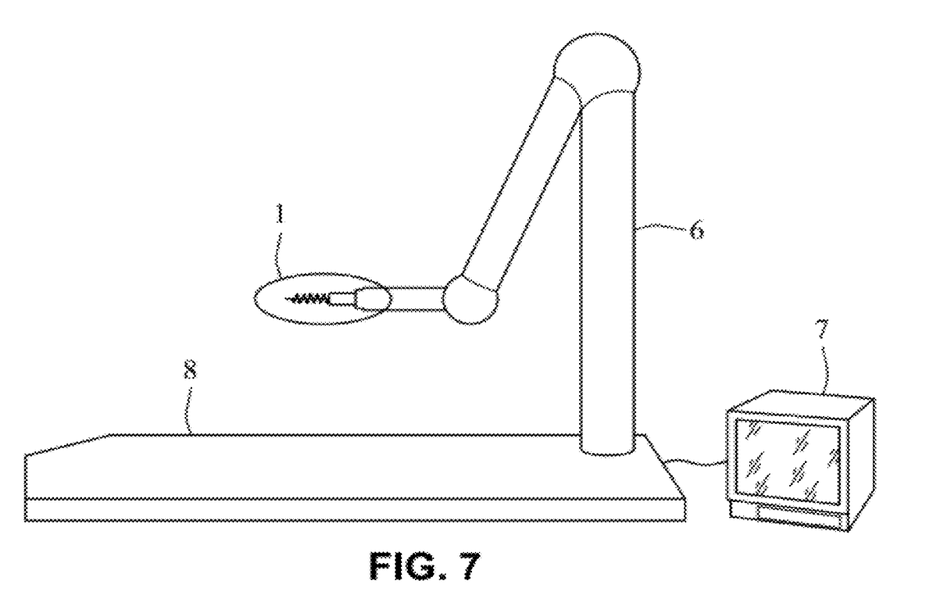
FIG. 7 illustrates an overview of a surgical system comprising the medical device according to the present invention which is linked to a robotic arm and controlling means, and is fixed via the robotic arm to a surgical table or floor.

Advantageously but not necessarily, said device 1, as shown on FIG. 7, is in fact part of an assembly comprising also controlling means. Said controlling means may advantageously comprise a robot supported by a robotic arm 6 and piloted by computerising means 7, for controlling the operating state of the device 1.

The main body 2 and the stabilizing means 3 of the device 1 according to the invention have both a distal end, 20 and 30 respectively, and a proximal end 21 and 31 respectively.

The main body 2 is attached by its distal end 20 to the proximal end 31 of the stabilizing device 3, while its proximal end 21 can be attached to the robotic arm 6 of a robot.

The stabilizing means 3 is configured so as to allow its positioning at the outer surface of a target volume or organ in operating conditions, thereby contributing to the stabilisation of said target relatively to the device. For example, as shown on FIG. 1 and more detailed on FIG. 4, the stabilising means 3 may have a hollow cylindrical shape, with its walls delimiting an internal cavity 33 and a more external cavity 32.

The bipolar electrode 10, as further shown on FIG. 1, comprises a central needle 5. The needle 5 of the electrode 10 has a distal end 51 in the form of a tip so as to be able to penetrate inside a target tissue volume in operating conditions. Said needle 5 has also a proximal end 52, by which the needle 5 of the electrode 10 may be linked to an external radio-frequency (RF) source or generator so as to constitute a passive pole of the electrode 10 that is to say in operating conditions an electric or electromagnetic current provided by the radiofrequency generator may flow towards it.

The bipolar electrode 10 also comprises at least two helical or coiled elements 4', 4", . . . which are concentric helices able to surround the needle 5 and to form a cage-like structure around said needle 5, when deployed according to a working configuration (see hereafter). Each of said helices is defined by its diameter D and its length L. Another feature characterizing an helix is its pitch P.

Preferably, the diameter D of all the helical elements 4', 4", . . . are a multiple of a distance d, d being the diameter of the smallest helix, i.e. the distance between the smallest helical elements 4' and the main axis A of the needle 5.

According to the present invention, this distance d can be different depending on the embodiment of the medical device 1 and on the target organ (prostate, kidneys, breast, . . . ) to be treated and its anatomical features (size and shape, namely).

Each of the helical elements 4', 4", . . . of the electrode 10 has a distal end 41', 41", . . . and a proximal end 42', 42", . . . . The proximal ends 42', 42", . . . are linked to the external radio frequency (RF) generator, while the distal ends 41', 41", . . . are free.

Figure 3A:
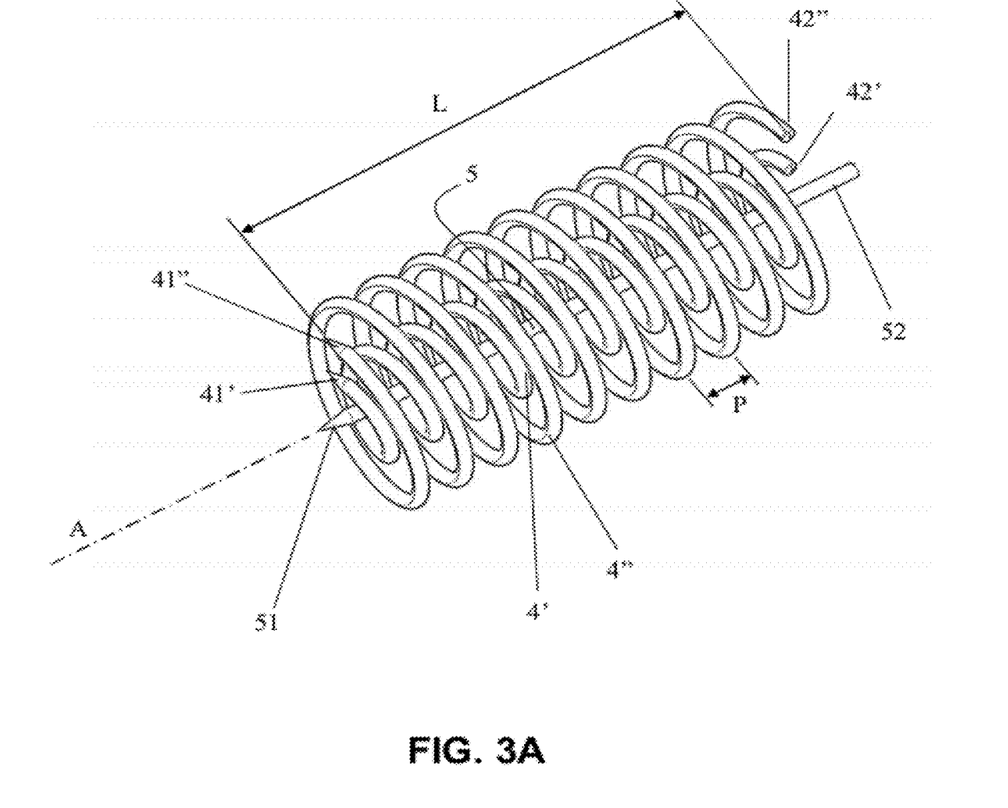
FIG. 3a represents a detailed view of the bipolar electrode comprised in a device according to the invention, and including a needle shaped central pole and two cage-like helical poles.
Figure 3B:
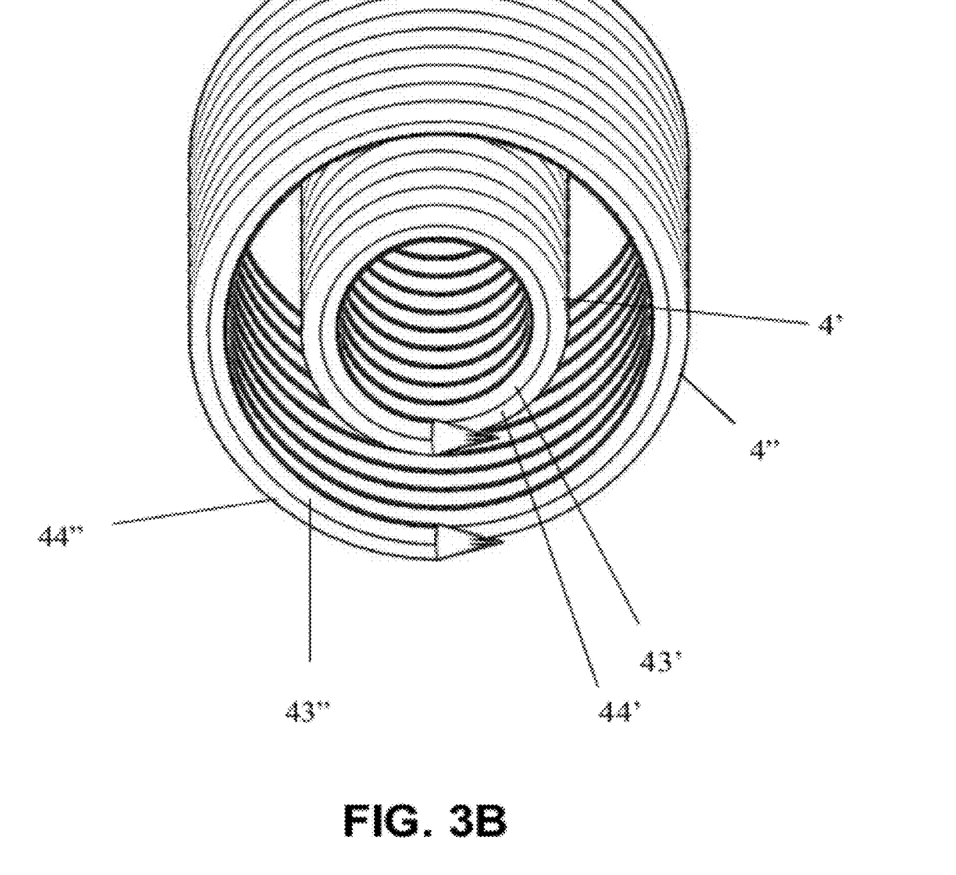
FIG. 3b represents a front view of said cage-like helical poles.

As illustrated in FIG. 3b, for each of said helical elements 4', 4" . . . , an internal face 43', 43", . . . arranged towards the central needle 5 and an external face 44', 44", . . . arranged towards the outside environment can be defined.

According to a first preferred embodiment of the invention, only the internal faces 43', 43", . . . of said helical elements are activable separately and independently by the controlling means so that the internal face of one of said helices may constitute the active pole of the electrode 10, that is to say in operating conditions, an electric or electromagnetic current flows from it to the area of the bipolar electrode forming the passive pole.

On the contrary, each of the external faces 44', 44", . . . of the helical elements 4', 4", . . . are susceptible to form the passive pole of the electrode 10, so that in operating conditions an electric or electromagnetic current may flow from the active pole to the external face of one of the helices forming the passive pole.

In this first embodiment, the passive pole of the bipolar electrode 10 may also be formed by the central needle 5.

According to a second preferred embodiment of the invention, the helices are activable separately and independently by the controlling means on both their internal faces 43', 43", . . . and their external faces 44', 44", . . . so that one of said helix may constitute the active pole of the electrode 10, that is to say in operating conditions, an electric or electromagnetic current flows from it to the area of the bipolar electrode forming the passive pole.

In said second embodiment, the passive pole may be formed either by another helix of smaller diameter than the helix forming the active pole, or by the central needle 5.

It should be noted that the composition of the helices is adapted according to the activation scheme to be achieved. For example, in the hereabove mentioned second embodiment, wherein the helices are activable on both faces, the helices are entirely made of an adequate biocompatible and conducting metallic component. Comparatively, in the first embodiment, wherein the helices are activable only on their internal face, only said internal face is made of such a metallic conducting component, while the external faces of the helices is made of an adequate biocompatible and isolating polymeric component.

It should be noted that in both said first and second embodiments, the helices are activable either along their full length or only along at least one fraction of said length. It means that in the case wherein the helices are activable only on one or more fractions of their length an adequate isolation pattern of the helices has to be provided.

Figure 2:
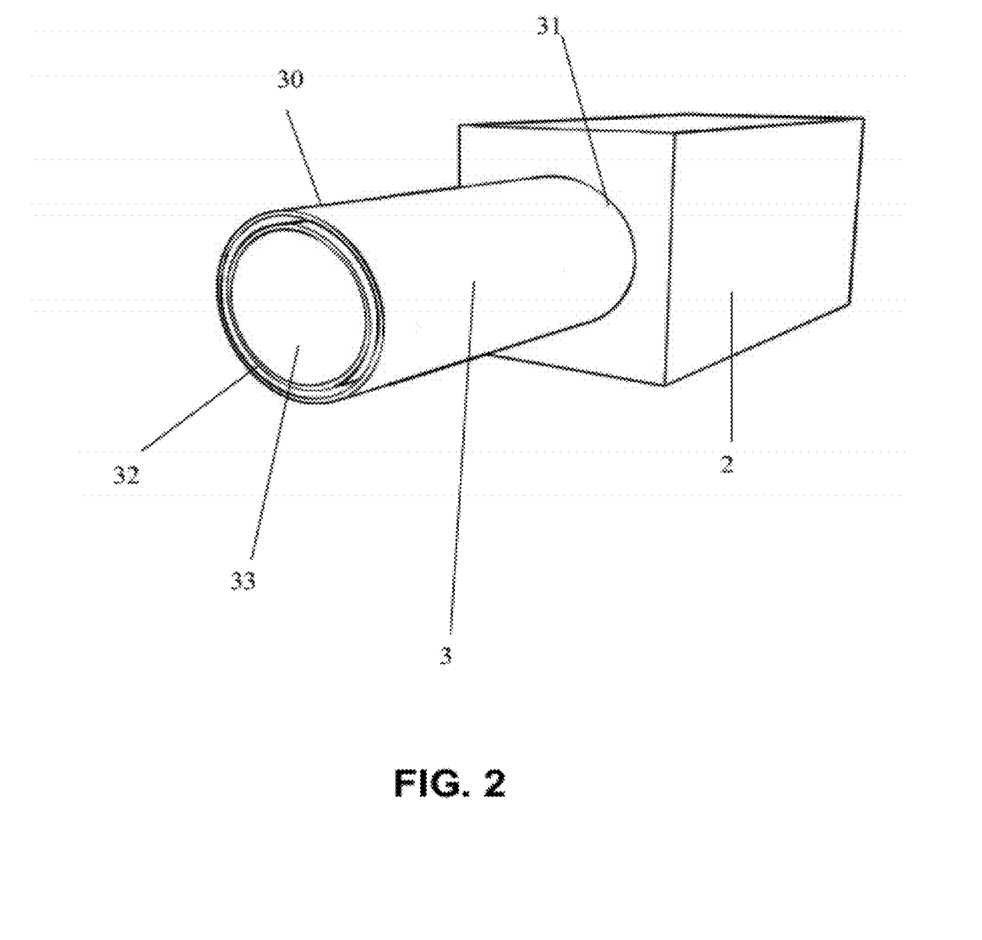
FIG. 2 represents said medical device in rest configuration (pre-operative position with the electrode folded-up inside the main body of the device).

According to the invention, the device 1 may adopt at least one rest configuration as shown on FIG. 2, wherein the bipolar electrode 10 (needle 5+helices 4', 4", . . . ) is folded up inside the main body 2 and the stabilising means 3 (bipolar electrode hidden from the outside environment) and wherein the bipolar electrode 10 cannot be activated (is unactivable).

It means that in said rest configuration, both the ends 41', 41", . . . and 42', 42", . . . of the helices 4', 4", . . . are folded up inside the stabilizing device 3 and main body 2.

Moreover, in rest configuration, the medical device 1 as a whole presents different degrees of freedom.

Figure 4:
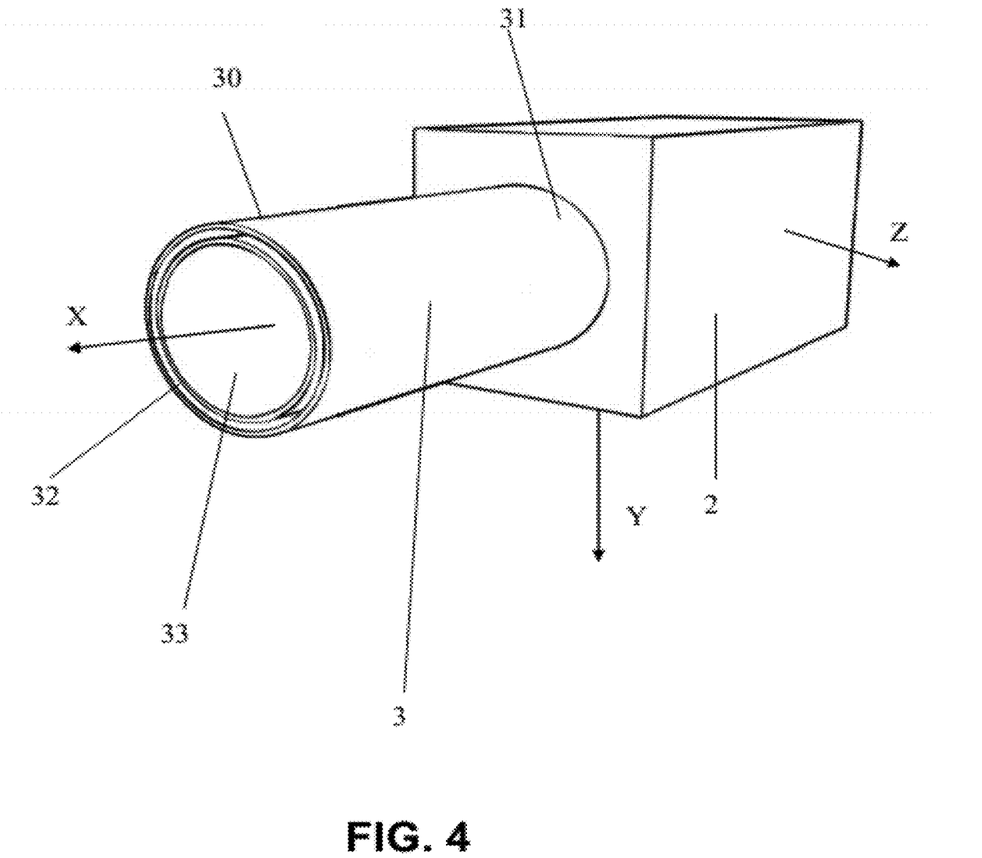
FIG. 4 represents the main body of a medical device provided with its stabilizing means, and shows the different degrees of freedom for said medical device.

More precisely, as illustrated on FIG. 4, in the referential system (O, X, Y, Z) centred at the centre O of the main body 2 of the medical device 1, the following degrees of freedom are associated to the medical device 1:

rotation around the Z axis;
rotation around the Y axis;
translation along the X axis;
translation along the Y axis;
translation along the Z axis.

According to the invention, the device 1 may also adopt at least one working configuration, wherein the bipolar electrode 10 (needle 5 and at least one helix 4') protrudes outside the stabilising means, beyond the distal end 30 of said stabilising means 3. The distal ends 41', 41", . . . of the helical elements 4', 4", . . . can be deployed out from the stabilizing device 3, while the proximal ends 42', 42", . . . of said helical elements remains inside the stabilizing device 3 and main body 2. In addition, in working configuration the bipolar electrode 10 is activable. It means that the bipolar electrode can be activated or not, depending on its activation state.

An example of such a working configuration is represented on FIG. 1.

In said working configuration, the device 1 is such that only the bipolar electrode 10 is able to move, the needle 5 presenting one degree of freedom, which corresponds to a translation along the X axis, while the helices 4', 4", . . . of the electrode 10 are able to perform a translation along the X axis and/or rotation around the X axis.

Figure 6:
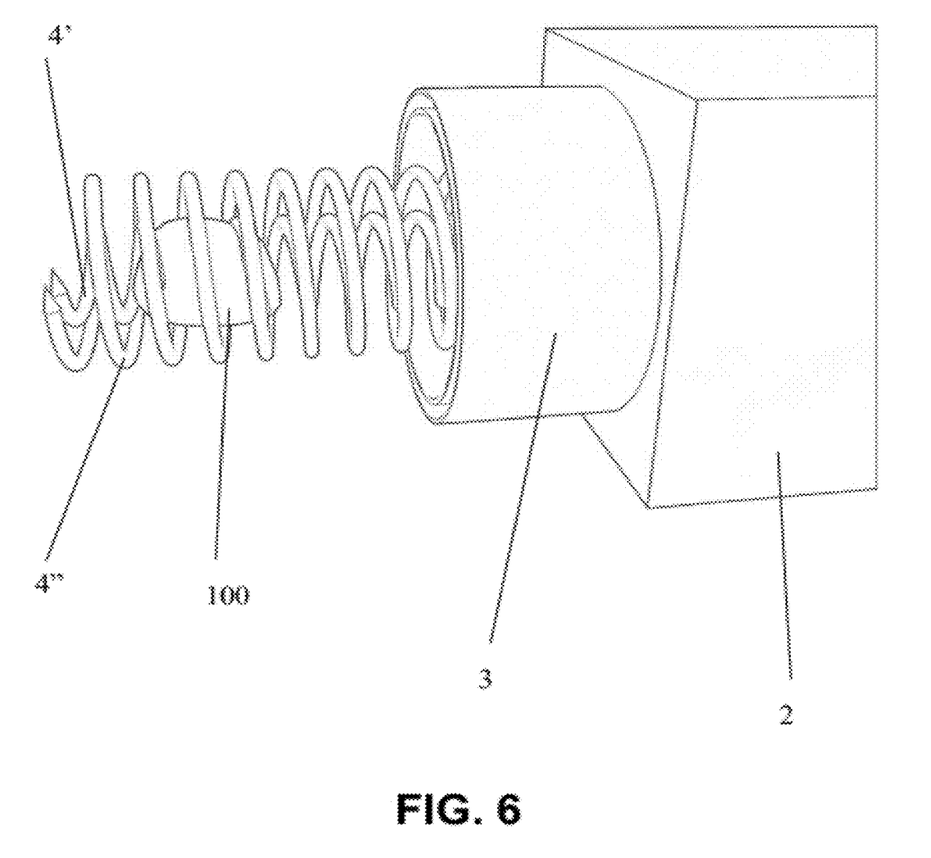
FIG. 6 represents a medical device according to the invention, with its bipolar electrode in a second operating position, wherein two helical poles are deployed around said target volume.

Therefore, the working configurations of the medical device 1 differ from each other at least by a different orientation of the bipolar electrode 10 that is to say of the needle 5 and/or of the helices 4', 4", . . . , relatively to the main body 2 in the referential system mentioned hereabove (see FIG. 6).

It should be noted that the combination of both movements (translation+rotation around X axis) allows in operating conditions the positioning of the helices 4', 4", . . . of the electrode 10 around a target volume (target tumor or tumoral target region) with one unique entry point into the organ, following a corkscrew-like movement.

It should also be noted that the medical device 1 of the invention is conceived in such a manner that the movements of the main body 2 and of the stabilisation means 3 are locked before the needle 5 and the helices 4', 4" . . . of the electrode 10 can move. It means that in working configuration, the main body 2 and the stabilising means 3 cannot move. In addition, it is also possible to lock the robotic arm 6 of the assembly.

All these movements of the medical device 1 are done with a near millimeter precision, under the control of the controlling means.

Advantageously, all these movements are done via the robotic arm 6 of a robot and by means of different activators and micro-activators.

Preferably, the diameter D of all the helical elements 4', 4", . . . are a multiple of a distance d, d being the diameter of the smallest helix, i.e. twice the distance between the smallest helical elements 4' and the main axis A of the needle 5.

These activators and micro-activators necessary for the described movements of the medical device 1 can be of several types, including electrostatic, magnetic, piezo-electric, thermic, shape memory allow (SMA), fluidic and electrorheologic ones An important feature of the present device is the fact that the configuration the device 1, as well as the activation state of the bipolar electrode are controllable by the controlling means.

Furthermore, it should be noted that the composition and dimensions of the different elements of the device 1 i.e. the main body 2, the stabilizing device 3, the needle 5 or other equivalent anchoring member and the helices 4', 4", . . . of the electrode 10 are compatible with their technical use (the prostate, kidneys, adrenal glands, lungs, etc. . . . ), in particular in terms of biocompatibility, and can be easily adapted from the present description by the man skilled in the art.

In practice, the anchoring member (needle 5) and the helices 4', 4", . . . always work together so as to form the bipolar electrode 10, with the electric or electromagnetic current flowing from the more external pole (the active pole) to the more internal pole (passive pole) as defined hereabove.

This movement of the current from the periphery to the center of the medical device allows a better control of the region to be destroyed by heating. The present apparatus and associated process thus prevent undesirable heating of the surrounding tissues located immediately outside the active helix.

Figure 5:
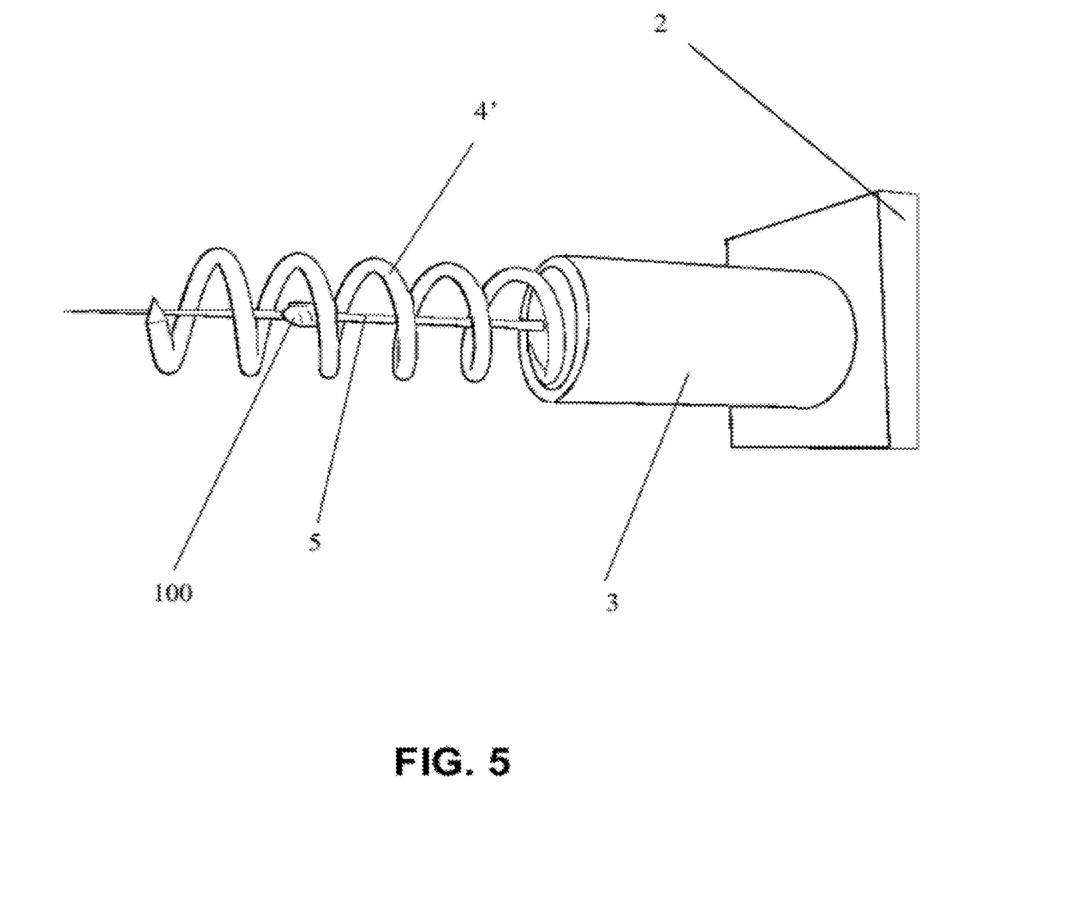
FIG. 5 represents a medical device according to the invention, with its bipolar electrode in a first operating position, wherein the needle-like pole arranged inside a target volume and one helical pole deployed and arranged around said target volume.

In a first case, as illustrated in FIG. 5, wherein the target volume 100 (target tumor or tumoral region) is sufficiently small, the controlling means and thus possibly the robot, control the different elements of the device in such a manner that in the working configuration the needle 5 and the smallest helix 4' protrude outside the main body and stabilising means 3, the needle 5 penetrating inside the target volume 100 and the helix 4' wrapping said target volume 100, while helix 4" of greater diameter is folded up inside the main body 2 and stabilising means 3. The needle 5 operates as a passive pole, while the internal face 43' of the smallest helix 4' operates as the active pole and the external face 44' of said helix 4' remains inactive i.e. is not activated by the RF external generator.

In a second case, as illustrated in FIG. 6, the target volume 100 to be destroyed by heating is bigger than the diameter of the smallest helix 4'. Therefore, the controlling means and thus possibly the robot control the device in such a manner that the needle 5 as anchoring member and the helices 4', 4" protrude outside the main body 2 and stabilising means 3, the needle 5 and the helix 4' penetrating inside the target volume 100 and the helix 4" wrapping said target volume 100. The passive pole is the external face 44' of the smallest helix 4' and the active pole is the internal face 43" of the immediately bigger helix 4". (The other faces of the two helices 4' and 4", i.e. the internal face 43' of the smallest helix 4' and the external face 44" of the immediately biggest helix 4" are inactive, i.e. not activated by the external RF generator).

Similarly, if necessary, it is possible to destroy even bigger target volumes 100 by deploying and activating through the controlling means other helices 4''', 4'''' . . . , of bigger diameter as mentioned previously. So, the technical features of the device 1, and namely the number of helices 4', 4", 4''', 4'''', . . . in the device 1, depend on the conception of said device 1 and can be adapted according to one or more target organs and their anatomical characteristics and specificities.

It is thus possible to adapt the diameter of the helix to the volume of the target volume by selecting the appropriate external helix.

In practice, the use of the device and assembly according to the invention can be done according to a process comprising the following steps, in the embodiment wherein the controlling means comprise a micro-robot.

Before the surgery, the robot orders the 3D navigation system to take informations such as images about the tumor and target organ. Said informations are treated by the robot (controlling means) so as to determine a surgical protocol (sequence in time of movements of the device 1, number of helices to be protruding, definition of the passive and active poles, intensity and length of the activation of the electrode, . . . ) according to parameters including anatomical features (position, shape, size, . . . ) of the tumor and organ to be treated.

During the surgery, the surgeon introduces the medical device in rest configuration inside the patient using the 3D-navigation system which allows the monitoring in real time of the position of both the medical device and the target organ. Once the target organ is reached, the surgeon positions approximately the medical device relatively to the target organ and starts the automatic operating of the robot according to the predefined surgical protocol. The surgeon lets the robot operating but he has the possibility to monitor the whole surgical procedure through the navigation system.

Using its robotic arm 6 the robot readjust the position of the device, which is still in rest configuration, relatively to the target organ and namely the precise positioning of the stabilizing means 3 at the outer surface of the target organ so as to align the main axis X of the medical device 1 with the tumoral region 100 to be destroyed by heating.

The stabilizing device 3 thus gives to the navigation system an important fixed point and allows an easier penetration of the electrode 10 into the patient's skin or organ's surface.

The robot then orders the configuration change of the device into the working configuration, with the deployment of the needle 5 until it reaches the tumor or tumoral region center and the deployment of the smallest helix 4' in such a manner that said helix 4' may wrap the tumor or tumoral region 100 to be destroyed. The actuators responsible for this deployment and the degrees of freedom have been described above.

The robot then activates the poles of the electrode 10 as described above in the first case.

When the tumor or tumoral region 100 is bigger than the diameter of the smallest helix 4', the robot orders the deployment of one or more additional helices 4", 4''', 4'''', . . . so as to completely wrap the tumoral region to be destroyed by heating. The activation of the helices is done as in the second case described above.

The tumoral regions wrapped by the helical cage-like helices 4', 4", 4''', . . . of the electrode 10 are thus destroyed by heating with no damage to surrounding tissues and only a few penetration points in the patient's skin or on the surface of the organ (the prostate, kidneys, adrenal glands, lungs, etc. . . . ). The present device 1 thus requires a minimally invasive intervention.

It should be noted that the robot 1 with its robotic arm 6 is provided with securing means activable in case of abnormalities for interrupting the working of the robotic system so that the surgeon may continue manually the surgical procedure.

In this manner, the medical device of the present invention offers all the guarantees of security for the patient.

As illustrated hereabove, the medical device 1 and method according to the present invention thus offer undeniable advantages over the state of the art.

The invention claimed is:

1. A medical device adapted for the ablation of a target volume inside an anatomical organ, said medical device comprising a main body, a stabilizer for stabilising the medical device relatively to the organ and heating means in the form of a bipolar electrode comprising parts activatable by an external radiofrequency generator for heating said target volume, wherein said bipolar electrode consists of a first element having the form of a straight needle, and a second element having the form of two concentric rigid helices of predetermined diameters and length, and arranged concentric around the straight needle, said first and second elements being independently deployable between first retracted positions inside the stabilizer and second protruding positions outside the stabilizer, wherein the medical device has at least two distinct operational modes with each of the two helices being activatable independently of one another to form a first pole, and a second pole being formed, in a first operational mode, by the straight needle, with the helix other than the helix forming the first pole being inactive, and in a second operational mode, by the helix other than the helix forming the first pole, with the straight needle being inactive; and wherein during operation in either of the first or second operational modes, the external radiofrequency generator activates an active outermost one of the helices and destroys the target volume wrapped by the active outermost one of the helices and destroys the target volume wrapped by the active outermost one of the helices in bipolar mode, while at the same time preserving surrounding tissues located immediately outside of the active outermost one of the helices.

2. The medical device according to claim 1, wherein the helices are activatable at least on one fraction of their length.

3. The medical device according to claim 1, wherein the helices are activatable on their full length.

4. The medical device according to claim 1, wherein in a rest configuration, said medical device has the following degrees of freedom in a referential system (O, X, Y, Z) centred at the centre of the main body:
Rotation around the Z axis;
Rotation around the Y axis;
Translation along the X axis;
Translation along the Y axis;
Translation along the Z axis.

5. The medical device according to claim 1, wherein in a working configuration, the medical device is such that the straight needle of the bipolar electrode has one degree of freedom in a referential system (O, X, Y, Z) centred at the centre of the main body corresponding to a translation along the X axis, while the helices have two degrees of freedom, one corresponding to a translation along the X axis, and the other to a rotation around the X axis.

6. The medical device according to claim 5, wherein in the working configuration any translation or rotational movement of the main body and of the stabilizer is blocked.

7. The medical device according to claim 1 being conceived such that the positioning of the different elements of said medical device relatively to the target volume and relatively to each other and the activation state of said parts of the bipolar electrode are able to be controlled by controlling means.

8. The medical device according to claim 7, wherein the controlling means comprise a robot.

9. The medical device according to claim 8, wherein said robot is coupled to a 3D-navigation system and to a computer.

10. The medical device of claim 1, wherein the medical device is coupled to a controlling means to provide a surgical assembly.

11. The medical device according to claim 10, wherein said controlling means comprise a robot.

12. A medical device according to claim 11, further comprising a 3D navigation system and/or a computer and/or interfacing means.

13. The medical device of claim 1, wherein the straight needle and the concentric rigid helices are entirely made of one or more biocompatible materials.

14. The medical device of claim 1, wherein in operation conditions the concentric rigid helices and the straight needle are configured to remain in position relative to the target volume, such that a zone of ablation is confined to between the first pole and the second pole.

15. The medical device of claim 1, further comprising a controller configured with the at least two distinct operational modes, the controller controlling the operation of the bipolar electrode.

16. The medical device of claim 1, wherein the straight needle and each of the two concentric rigid helices have proximal ends configured to be linked to the external radiofrequency generator, such that in each operational mode only two of the proximal ends are linked to the external radiofrequency generator.

17. The medical device of claim 1, wherein the two helices are independently deployable, and in the first operational mode the inactive helix is kept in the retracted position.

18. A process for the destruction of a target volume inside an anatomical organ by radiofrequency ablation technique using a medical device or a surgical assembly incorporating the medical device, said process comprising the following steps:
 determining parameters comprising at least the anatomical features of a target volume to be treated;
 on the basis of said parameters, defining two concentric helices of predetermined diameters and length and a straight needle concentric to the two concentric helices to use in a bipolar electrode, defining a mode of activation of the bipolar electrode by selecting between the two helices which one to activate as a first pole, and by selecting a second pole to be formed by the straight needle or the other helix than the helix forming the first pole, while keeping the other one of the straight needle and the other helix inactive, and defining an intensity and time of activation of said bipolar electrode;
introducing at least part of said medical device inside the patient;
once a target organ is reached, positioning the medical device relatively to the target volume;
 performing a treatment procedure of the target volume following the predetermined parameters and activating the bipolar electrode according to the defined mode of activation to destroy a volume of tissue wrapped by an active outermost one of the helices, while at the same time preserving tissue surrounding the active outermost one of the helices.

19. The process of claim 18, wherein the treatment of target volume is of an anatomical organ selected from the group consisting of kidneys, lungs, liver, breast, prostate and brain.

20. The process of claim 18, wherein the bipolar electrode is activated according to a sequence of selection and activation comprising firstly selecting a helix having the smallest diameter of the two helices as the first pole and selecting the straight needle as the second pole and activating to destroy a first target volume and subsequently selecting a helix having the larger diameter as the first pole and selecting the helix having the smallest diameter as the second pole and activating to destroy a second target volume surrounding the first target volume.

21. The process of claim 18, wherein the treatment procedure comprises keeping the helices and the straight needle in position relative to the target volume during at least a part of the treatment procedure, such that a zone of ablation is confined to a volume wrapped by the active outermost one of the two helices.

22. A process for the destruction of a target volume inside an anatomical organ by radiofrequency ablation technique using a medical device or a surgical assembly incorporating the medical device, said process comprising the following steps by means of a three dimensional navigation system:
 establishing a surgical protocol according to different parameters including the anatomical features of the target volume to be treated, said surgical protocol defining a sequence and a type of movements of the medical device and of its different elements, at least two concentric helices of predetermined diameters and length and a straight needle concentric to the at least two concentric helices to use in a bipolar electrode, a mode of activation of the bipolar electrode by selecting between the at least two helices which one to activate as a first pole, and by selecting a second pole to be formed by the straight needle or another one of the at least two helices other than the helix forming the first pole, while keeping non-selected ones of the straight needle and the at least two helices inactive, an intensity and a time of activation of said bipolar electrode;
 manually introducing at least part of said medical device inside the patient and approximately positioning said device relatively to the target volume;
 starting an automatic operating of the three dimensional navigation system so as to perform a surgical procedure under automatic control following the established surgical protocol;
 activating the bipolar electrode according to the defined mode of activation to destroy a volume of tissue wrapped by an active outermost one of the at least two helices, while at the same time preserving tissue surrounding the active outermost one of the at least two helices;
 monitoring the surgical procedure and restoring a manual control on the device, in case of security problems.

23. The process of claim 22, wherein the treatment of target volume is of an anatomical organ selected from the group consisting of kidneys, lungs, liver, breast, prostate and brain.

24. The process of claim 22, wherein the bipolar electrode is activated according to a sequence of selection and activation comprising firstly selecting a helix having the smallest diameter of the at least two helices as the first pole and selecting the straight needle as the second pole and activating to destroy a first target volume and subsequently selecting a helix having a larger diameter as the first pole and selecting the helix having the smallest diameter as the second pole and activating to destroy a second target volume surrounding the first target volume.

25. The process of claim 22, wherein the surgical procedure comprises keeping the at least two helices and the straight needle in position relative to the target volume during at least a part of the surgical procedure, such that a zone of ablation is confined to a volume wrapped by the active outermost one of the at least two helices.

* * * * *